United States Patent [19]

Safarian et al.

[11] Patent Number: 5,677,422
[45] Date of Patent: Oct. 14, 1997

[54] METHOD FOR MAKING A POLYPEPTIDE DERIVATIVE

[75] Inventors: Zara Safarian, Brea; Hann-Ping Wang, Yorba Linda, both of Calif.

[73] Assignee: Beckman Instruments, Inc., Fullerton, Calif.

[21] Appl. No.: 701,560

[22] Filed: Aug. 22, 1996

Related U.S. Application Data

[63] Continuation of Ser. No. 319,448, Oct. 5, 1994, abandoned.
[51] Int. Cl.$^6$ .................................................. C07K 1/107
[52] U.S. Cl. ............................................. 530/345; 530/402
[58] Field of Search .................................... 530/345, 402

[56] References Cited

U.S. PATENT DOCUMENTS

| | | | |
|---|---|---|---|
| 4,057,685 | 11/1977 | McIntire | 536/18 |
| 4,220,722 | 9/1980 | Rowley | 435/188 |
| 4,474,694 | 10/1984 | Coco | 260/123.5 |
| 4,931,544 | 6/1990 | Katre | 530/351 |

FOREIGN PATENT DOCUMENTS 62-195400  4/1987  Japan.

OTHER PUBLICATIONS

Meighan, et al., Hydridization of Enzymes, I, vol. 9, No. 5, Mar. 3, 1970, pp. 1163–1175.

Habeeb, et al., "Molecular Structural Effects Produced in Proteins by Reaction with Succinic Anhydride", BBA, vol. 29, pp. 387–393 (1958).

Habeeb A.F.S.A., et al., "Enzymic and Immunochemical Properties of Lysozyme", *Immunochemistry*, vol. 8, pp. 1047–1059 (1971).

Klapper, M. H., et al., "Acylation with Dicarboxylic Acid Anhydrides", Methods in Enzymology, vol. 25, pp. 531–536 (1972).

Shiao, D.D.F., et al., "Modification of Protein Properties by Change in Charge", Eur. J. Biochem, vol. 29, pp. 377–385 (1972).

Hettiarachchi, K., et al. "Capillary Electrophoresis Anaysis of Concanavalin A and its Succinyl derivative", J. of Pharm. and Biomed. Analysis, vol. 9, pp. 835–841 (1991).

Klapper, M. H., et al, "Hybridization of Chemically Modified Proteins", Methods in Enzymology, vol. 25, pp. 536–541 (1972).

Klotz, I. M., "Succinylation", Methods in Enzymology, vol. 11, pp. 576–581 (1967).

*Primary Examiner*—Cecilia J. Tsang
*Assistant Examiner*—Anish Gupta
*Attorney, Agent, or Firm*—William H. May; Gary T. Hampson; Sheldon & Mak

[57] ABSTRACT

A method for making a homogeneous succinylated polypeptide is disclosed. The method can be carried out by adding a succinyl-containing compound to a polypeptide solution, followed by raising the pH of the polypeptide solution to a pH of between about pH 10 to pH 12.5. The succinylation reaction between the succinyl-containing compound and free amino groups of the polypeptide is essentially complete upon raising the polypeptide solution pH to the alkaline pH.

18 Claims, 2 Drawing Sheets

METHOD FOR MAKING A POLYPEPTIDE DERIVATIVE

This is a continuation of application(s) Ser. No. 08/319,448 filed on Oct. 5, 1994, now abandoned.

BACKGROUND

The present invention is related to a method for making a polypeptide derivative. In particular, the present invention is related to a method for making a homogeneous acylated polypeptide derivative.

A polypeptide can be a naturally occurring or artificially made molecule comprising two or more peptide bonds. Thus, a polypeptide can include compounds classified as or referred to as polyamino acids, protein hormones, antibodies, antigens, histones, protamines, albumins, globulins, as well as various scleroproteins, phosphoproteins, mucoproteins, chromoproteins, lipoproteins, nucleoproteins, glycoproteins and derivatives and metabolites thereof.

A polypeptide can be acylated by bonding an acyl group[1] to a reactive or free functional group of the polypeptide. A reactive group of a polypeptide is often an amino group, a hydroxyl or thiol group, which is so positioned on the polypeptide molecule that it is accessible for electron transfer from and covalent bonding with a carbonyl group of the acylating compound.

[1] An acyl group can be represented as:

Various anhydride compounds, such as succinic anhydride, can be used to acylate a reactive functional group of a polypeptide. Thus, succinylation is an acylation reaction by which a succinyl group covalently attaches to a reactive group of a polypeptide. Polypeptide succinylation can be carried out by reacting a succinyl-containing compound with a polypeptide dissolved in solution. A polypeptide solution can contain many separate though chemically identical polypeptide molecules.

A succinylated polypeptide can have considerable utility for the study of protein dissociation, protein hybridization, mapping of amino acid constituents, peptide sequencing, and for the purpose of introducing various functional groups into a polypeptide.

The utility of a succinylated polypeptide is directly related to both the degree or extent of succinylation achieved (i.e. how many of the reactive groups per polypeptide molecule have become succinylated) and the difference in the degree of succinylation achieved between different polypeptide molecules in the same solution. When the difference in the degree of succinylation between different polypeptide molecules is low, the succinylation can be referred to as homogeneous. When the difference in the degree of succinylation between different polypeptide molecules is high, the succinylation can be referred to as heterogeneous. Generally, a high degree of succinylation and a homogeneous succinylation of a polypeptide is desired. A low degree or extent of succinylation (i.e. less than about 10% of the reactive functional groups per polypeptide molecule in the polypeptide solution become succinylated) can result in product with limited utility for protein studies or functional group introduction. Additionally, electrophoretic analysis of a heterogeneous modified protein can result in an electropherogram with multiple poorly defined peaks. Such an electropherogram is difficult if not impossible to interpret and can thereby impede medical therapy, diagnosis and research.

A high degree of succinylation can be said to have occurred when about 30% of the reactive functional groups per polypeptide molecule in a polypeptide solution have become succinylated. Additionally, a homogeneous succinylation can be said to have occurred when the degree of succinylation between different polypeptide molecules in the solution differs by no more than about 20%. A homogeneously succinylated polypeptide resolves as a single major peak when a sample of the succinylated polypeptide solution is subjected to capillary electrophoresis.

Currently used polypeptide succinylation methods have numerous deficiencies and drawbacks. Thus, known polypeptide succinylation methods result in heterogeneously modified polypeptide. An insensitive or low resolution procedure, such as gel electrophoresis, can appear to indicate, due to the appearance of a single major electropherogram peak, that a homogeneously modified polypeptide is made using known succinylation procedures. A more sensitive procedure such as capillary gel electrophoresis can often show that in fact a heterogeneously modified polypeptide has been made, by resolving the succinylated polypeptide product into two or more major electropherogram peaks.

Known polypeptide succinylation methods are believed to result in heterogeneously modified polypeptide because succinylation of a polypeptide in solution is carried out while maintaining the polypeptide solution at a physiological pH of between about pH 6 to about pH 8. The succinylation is carried out at a physiological pH because at a non-physiological pH the succinyl-containing compound used to succinylate the polypeptide can exist in an unreactive form and the polypeptide can denature.

Unfortunately, at a physiological pH a significant number of a polypeptide's reactive functional groups can be in an unreactive cationic form. Thus, the amino groups of a polypeptide can be in the unreactive ammonia ($R-NH^+_3$) form.

Besides resulting in heterogeneously modified polypeptides, known polypeptide succinylation methods are slow. Thus, a protein succinylation method can require an incubation period of at least about thirty minutes subsequent to addition of the succinyl-containing compound to the polypeptide solution to ensure that the succinylation reaction has run to or near completion.

Succinic anhydride is the succinyl-containing compound typically added to a polypeptide solution to succinylate a polypeptide. Additionally, sodium hydroxide is typically used as an alkaline compound to bring succinic anhydride-polypeptide solution to, and maintain it at, a physiological pH. Known succinylation methods are carried out by first adding a portion of the total succinic anhydride to be used to the polypeptide solution. A portion of the total sodium hydroxide to be used is then combined with the succinic anhydride-polypeptide solution. The pH of the solution is measured and another portion of the total amount of succinic anhydride to be used is added to the solution, followed by pH measurement, and addition of another portion of the total amount of sodium hydroxide to be used.

Four or five separate aliquots of a succinic anhydride and four or five separate aliquots sodium hydroxide are added in this fashion until all of the desired amounts of succinic anhydride and of sodium hydroxide have been added to the polypeptide solution.

In such a known polypeptide succinylation method, an important objective is to maintain the pH of the polypeptide solution at a physiological pH (i.e. between about pH 6 and pH 8) to thereby prevent conversion (by hydrolysis) of the succinic anhydride into a less reactive, open chain, succinic acid form. It is for this reason that the succinic anhydride is added to the polypeptide solution first, followed by addition of the pH adjuster sodium hydroxide.

While such a method of sequential addition of multiple separate aliquots of succinic anhydride and sodium hydroxide does have the advantage of permitting the polypeptide solution's pH to be closely monitored and adjusted accordingly, it is laborious, time-consuming, error-prone, based upon trial and error measurements and can easily result in a deficiency or an excess of either of both of the amounts of succinic anhydride or of sodium hydroxide added to the polypeptide solution.

What is needed therefore is an improved method for making a homogeneous polypeptide derivative, such as a homogeneously succinylated protein.

SUMMARY

The present invention meets this need. The disclosed methods are fast, requiring no incubation period subsequent to a pH adjustment step, and result in homogeneously modified polypeptide.

A method for making a polypeptide derivative according to the present invention is carried out by adding a polypeptide modifier to a polypeptide solution, and adjusting the pH of the polypeptide solution to an alkaline pH. The polypeptide modifier comprises an acyl group. A solution of a homogeneous acylated polypeptide derivative results from this method. A second method within the scope of the present invention can include the additional steps of lowering the pH of the polypeptide solution and then repeating the addition, and pH adjustment steps.

The method is preferably carried out by adjusting the pH of the polypeptide solution to a pH of at least about 10, preferably to a pH of between about 10 and 12.5, more preferably to a pH of between about 11 and 12.5, and most preferably to a pH of between about 12 and 12.2. Additionally, the method requires that the polypeptide solution be maintained at a temperature of between about 4° C. and about 40° C., and preferably at a temperature of between about 15° C. and about 25° C.

When the disclosed method is practiced, a time period of between about thirty seconds and about thirty minutes elapses from initiation of the adding step to completion of the adjusting step. Preferably, a time period of between about five minutes and about twenty minutes elapses from initiation of the adding step to completion of the adjusting step, more preferably about ten minutes elapses, and most preferably a time period of between about ten seconds and about ten minutes elapses between initiation of the adjusting step and termination of the adjusting step. In a particularly preferred embodiment of the present invention, a time period of between about thirty seconds and about five minutes elapses between initiation of the adjusting step and termination of the adjusting step.

A detailed embodiment of a method within the scope of the present invention can be practiced by firstly adding a polypeptide modifier to a polypeptide solution to form a mixture, secondly adjusting the pH of the mixture to a pH of between about pH 10 and about pH 12.5, thereby obtaining a solution comprising a homogeneous polypeptide derivative, thirdly lowering the pH of the solution to a pH between about pH 6 and pH 7, fourthly adding additional polypeptide modifier to the protein solution, and fifthly raising the pH of the solution to a pH of between about pH 10 and about pH 12.5, to thereby obtain a solution comprising a homogeneous polypeptide derivative modified to a greater degree that the homogeneous polypeptide resulting from the second step above.

DRAWINGS

These and other features, aspects, and advantages of the present invention can become better understood from the following description, claims and the accompanying drawings where:

FIG. 1 also shows a method according to the present invention where the succinylation was carried out at pH 10.9 and at pH 12.2.

DESCRIPTION

Figure 1:
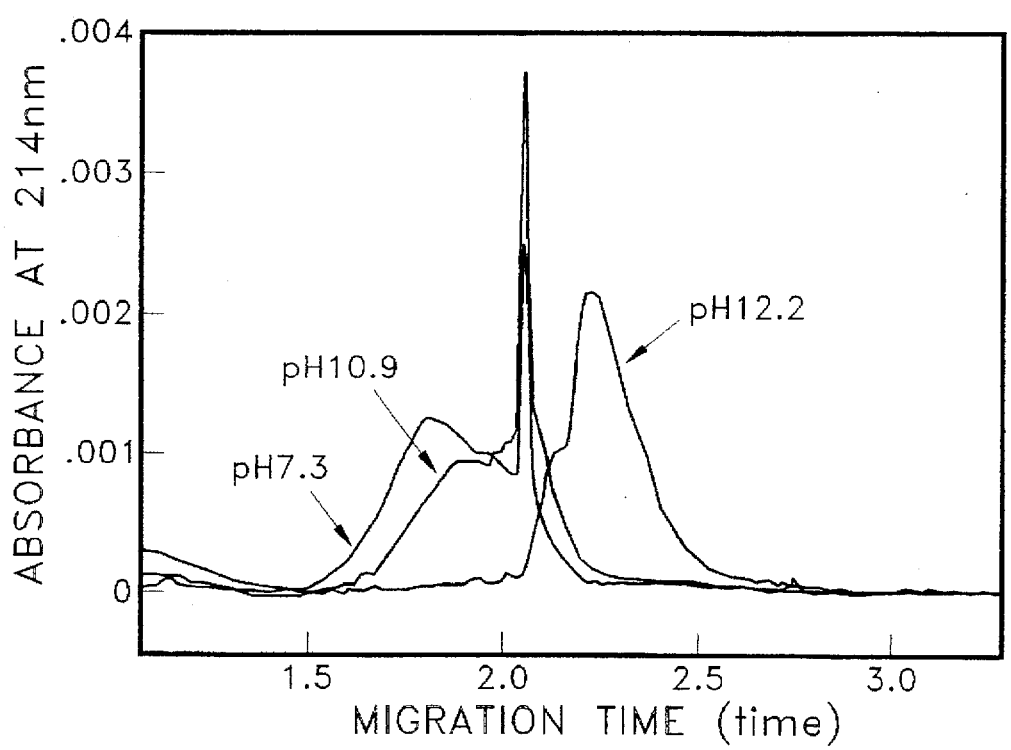
FIG. 1 is a capillary electropherogram resulting from analysis of an aliquot of a solution of anti-IgG antibody succinylated by a conventional procedure at pH 7.3.

The present invention is based upon the discovery that a homogeneous polypeptide derivative can be made by reacting a polypeptide solution with a polypeptide modifier at a sufficiently alkaline pH. The resulting polypeptide derivative has chemical homogeneity, as demonstrated by capillary electrophoretic analysis, and retains the immunological activity of the unmodified polypeptide.

A method within the scope of the present invention can be carried out by adding a modifier to a polypeptide solution. The addition step initiates a modification reaction between the modifier and reactive functional groups of the polypeptide. The next step of the method is to raise the pH of the polypeptide plus modified solution by adding an alkaline compound to the solution. In this first disclosed method only one pH adjustment step is carried out. The present invention also encompasses a second method in which there are two separate additions of a pH adjuster to the polypeptide solution. Both methods result in a homogeneous modified polypeptide which retains its immunological characteristics. The two addition step (or second) method is preferred because it results in a more highly modified, homogeneous polypeptide. The second method also results in better resolution, as demonstrated by capillary electrophoresis (see FIG. 2) of homogenous polypeptide from unmodified polypeptide, as compared to the first method.

In the one step modifier addition (or first) method, preferably at least about ten moles of the modifier are added to the polypeptide solution for each mole of polypeptide contained by the solution. A modifier:polypeptide molar ratio of less than about 10:1 can result in a significantly heterogeneous polypeptide production. This can occur because if the typical polypeptide is assumed to have twenty free amino groups per polypeptide molecule, and if the desired result is to modify at least one half or ten of the free amino groups per polypeptide molecule, then about ten moles of modifier per mole of polypeptide is required. Although ten moles of modifier is theoretically sufficient to achieve the desired fifty percent modification of the hypothetical polypeptide molecule, reaction kinetics typically dictate that more than the minimum ten moles of modifier per mole of polypeptide can be required to achieved the stated fifty percent minimum modification. Thus, more preferably, about twenty moles of the modifier is used for each mole of polypeptide in the solution because we have found that a molar ratio of about 20:1 results in substantially homogeneous polypeptide production.

Most preferably, at least about thirty moles of the modifier is used for each mole of polypeptide in the solution because at this molar ratio we have found that essentially all the polypeptide produced, as determined by capillary electrophoresis is homogeneous polypeptide.

In a particularly preferred embodiment of the one step method, between about thirty moles and about thirty-five moles of the modifier is used for each mole of polypeptide in the solution.

Adding an excessive amount of the polypeptide modifier to the polypeptide solution can result in an undesired reduction of the immunological activity of the polypeptide.

Preferably, between about 5% and about 30% of the free amino groups of a polypeptide are modified by the present method. Modification of less than about 5% of the free amino groups per polypeptide molecule introduces only a small charge alteration leading to less resolution by electrophoretic methods. Modification of more than about 30% of the free amino groups per polypeptide molecule can result in protein subunit dissociation or protein denaturation. More preferably, between about 10% and about 20% of the free amino groups of a polypeptide are modified by the present method, as we have found that such a range of free amino group modification provides modified and substantially undenatured polypeptides of high utility in immunological assays.

The pH adjustment step is terminated as soon as it is observed that the pH of the combined polypeptide modifier and polypeptide solution no longer changes and that the pH has therefore stabilized. Stabilization of the combined solution pH indicates that no further modification of the polypeptide by the polypeptide modifier is taking place.

The present invention also includes within its scope a second method by which two separate additions of the modifier are added to the polypeptide solution. In this method, the modifier:polypeptide molar ratio are preferably as set forth above for the first method. Additionally, the second method has a step during which more modifier is added to the polypeptide solution. Preferably, about twice as much modifier is added to the polypeptide solution during the second addition step as added to the polypeptide solution by the first addition step of this second method. Thus, in a preferred embodiment of the two step method, during the first modifier addition step about thirty to about thirty-five moles of the modifier are added to the polypeptide solution for each mole of polypeptide contained by the solution. During the second modifier addition step, about sixty moles to about seventy moles of more modifier are added to the polypeptide solution for each mole of polypeptide contained by the polypeptide solution. In the second preferred method the pH of the polypeptide solution is raised to about pH 12 subsequent to addition of the modifier, the pH is then lowered to a physiological pH and the pH is then raised to about pH 12 by again adding pH adjustor to the solution.

Subsequent to addition of the modifier to the polypeptide solution, the pH of the polypeptide solution is adjusted to facilitate reaction of the modifier with the polypeptide. Preferably, the pH of the polypeptide solution is adjusted to a pH of between about pH 10 and about pH 12.5. At a pH greater than about pH 12.5, the polypeptide may denature. At a pH lower than about pH 10, the reaction between the modifier and the polypeptide is slower and incomplete, resulting therefore in heterogeneous polypeptide reaction product. More preferably the pH is adjusted to a range between pH 11 and pH 12.5. Most preferably, the pH of the polypeptide solution, subsequent to addition of the modifier, is adjusted to a pH of between about pH 12 and pH 12.2.

The methods of the present invention are restricted to methods wherein addition of a polypeptide modifier to the polypeptide solution, is followed by the pH adjustment step. Thus, where succinic anhydride is used as the polypeptide modifier and sodium hydroxide is used as the pH adjuster, sodium hydroxide addition always follows addition of the succinic anhydride to the polypeptide solution. This addition sequence must be followed with the disclosed methods because adding a polypeptide modifier, such as a succinic anhydride, to an already alkaline (i.e. pH greater than about pH 8) polypeptide solution can result in immediate conversion of the polypeptide modifier to an unreactive form. Hence, the disclosed methods exclude a procedure wherein pH adjustment of the polypeptide solution to an alkaline pH precedes addition of the polypeptide modifier to the polypeptide solution.

In the disclosed methods, the pH of the polypeptide plus modifier solution is adjusted by slow dropwise addition of a pH modifier, such as a solution of sodium hydroxide (NaOH) or tetramethylammonium hydroxide ($C_4H_{13}NO.5H_2O$), to the polypeptide plus polypeptide modifier solution. Raising the pH in this manner can take from about twenty seconds to about five minutes depending on the volume of the polypeptide solution and the alkalinity of the liquid used to raise the pH of the modifier/polypeptide solution to the desired pH. The entire disclosed one addition step method can be carried out in about 10 minutes. A rapid shift to an alkaline pH can be injurious to a polypeptide modifier, such as a liquid succinic, maleic or acetic anhydride or an analog thereof and result in conversion of the polypeptide modifier to a less reactive form. A less reactive polypeptide modifier cannot be used to achieve a desired level of polypeptide modification within the indicated time periods.

A significant and key aspect of the present invention is the manner in which the succinyl-containing compound is added to the polypeptide solution and the manner in which the pH of the combined succinyl compound-polypeptide solution is adjusted to an alkaline pH.

In our invention, preferably, the total amount of the succinyl-containing compound to be added to the polypeptide solution is added to the polypeptide solution as a single batch of a succinyl-containing compound. It is also preferred that the total amount of the alkaline compound added to the combined succinyl compound-polypeptide solution is added slowly and dropwise as a single batch to the combined succinyl compound-polypeptide solution. Thus, a sequential addition of multiple separate aliquots of the succinic-containing compound and the alkaline compound is not practiced and is not preferred, although the alkaline compound is added in a slow dropwise manner.

Importantly, the disclosed method for adding the succinyl-compound and for adding the alkaline compound to the polypeptide solution does not result in either a significant conversion of the succinyl-containing compound to a less reactive chemical form, nor to any significant denaturation of the polypeptide.

Thus, the present invention achieves a polypeptide solution with an alkaline pH (with resulting excess of polypeptide $NH_2$ groups over less reactive and hence less easily succinylated polypeptide $NH_3^+$ groups) without, when succinic anhydride is used as the pH modifier, significant hydrolysis of the succinic anhydride present in the polypeptide solution to an open chain succinic acid form. From this balance and upon completion of the disclosed method, a homogeneous polypeptide results.

Upon adjustment of the pH to the desired alkaline pH, the reaction between the polypeptide modifier and the polypeptide is already essentially complete. Thus the present invention dispenses with the need for any incubation period subsequent to the pH adjustment step.

Raising the pH of the polypeptide solution to an alkaline pH is believed to facilitate polypeptide modification by causing —$NH_3^+$ to become —$NH_2$. The modification reaction can also be carried out, although less preferably, upon a free hydroxyl group of the polypeptide.

In a most preferred embodiment of the invention, the pH is raised to a pH between about pH 10 to pH 12.5 and the modification reaction is carried out at a temperature of between about 15° C. and 25° C. No further reaction time is required after completing the upward pH adjustment step and before removal of the modified polypeptide from the reaction solution.

The extent of polypeptide amino groups modified can be controlled by altering the molar ratio of modifier to polypeptide. Residual unreacted modifier can easily removed from the modified polypeptide solution by a brief ultrafiltration step. The polypeptide derivative made by the methods of the present invention is a homogeneous polypeptide derivative, as shown by capillary electrophoresis. Additionally, we have found that a modified antibody retains its immunologic activity, as demonstrated by immunocapillary electrophoretic analysis, subsequent to modification.

The polypeptide modifier is preferably added to the reaction solution in a liquid form to facilitate control of the modification reaction and to provide an improved lot-to-lot reproducability of the immunological characteristics of the modified protein The polypeptide solution is preferably maintained at a temperature of between about 4° C. and about 40° C., to facilitate a rapid reaction of the modifier with the polypeptide. A temperature greater than about 40° C. can damage the polypeptide modifier and cause the polypeptide itself to denature. A temperature lower than about 4° C. can cause the reaction to proceed very slowly. More preferably, the reaction is carried out at a temperature between about 15° C. and 25° C.

The present method can be practiced as a fast method for succinylating a polypeptide. Dialysis of the resulting succinylated polypeptide is not always required subsequent to the modification. A suitable polypeptide modifier is reactive with polypeptide free amino groups, and can lead to production of a polypeptide derivative which has a net charge at a neutral pH. A charged polypeptide can be detected by electrophoresis. A preferred polypeptide modifier is a succinyl compound such as a succinic anhydride compound. An alternate polypeptide modifier is a maleic compound such as a maleic anhydride compound. Maleic anhydride is less preferred because it can lead to production of an unstable polypeptide derivative.

The present method can be used to prepare a derivative of a polypeptide, such as a polyaminoacid, hormone, protein or a derivative thereof. The polypeptide to be modified must have a free amino group or less preferably a free hydroxyl group. By a free amino group it is meant that the polypeptide has the configuration polypeptide-$NH_2$.

EXAMPLES

The following examples set forth illustrations of various features and embodiments of the invention and are not intended to limit the scope of the claimed invention.

Example 1

(Protein Succinylation at pH 7.3)

A protein succinylation was carried out as follows. A one ml aliquot of an antibody solution in a protein diluent (10 mg antibody/ml protein diluent) containing 0.06 µmoles of antibody was prepared. The antibody used in all the Examples was a goat anti- human IgG polyclonal antibody. To the antibody solution there was added 1.8 µl solution of a 1.8 µmole solution of succinic anhydride in DMF (dimethyl formamide) (0.09 mg succinic anhydride/µl DMF) (Sigma). Thus the ratio of succinic anhydride to antibody used was 30:1.

The protein diluent used was a phosphate buffered saline buffer containing sodium chloride and $NaN_3$, and is available from Beckman Instruments, Inc., of Fullerton, Calif. as catalog number 663630.

The pH of the combined antibody and succinic anhydride solution was immediately adjusted to pH 7.3 by addition of 1N NaOH. The pH of the reaction solution was monitored using a pH meter, and was maintained at pH 7.3 by adding 1N NaOH dropwise throughout the reaction between the antibody and the succinic anhydride. Completion of the reaction was indicated by stabilization of the pH at 7.3. Once the pH became stabilized at 7.3, the reaction was allowed to continue for 30 minutes. Ultrafiltration was then performed on the reaction mixture to remove unreacted succinic anhydride, and to equilibrate the solution in the protein diluent. The succinylated antibody was analyzed by capillary electrophoresis and the results are set forth by FIG. 1

In all the Examples, the capillary electrophoretic procedure was as follows. A Beckman P/ACE™ 2000 CE System was used with modified "System Gold" software in conjunction with an IBM PS/2 computer. Electrophoresis was performed in untreated fused-silica capillary tubes (i.d. 27 µm, 20 cm long) with polyimide outside coating to protect the capillary from breakage (Polymicro Technologies, Inc., Phoenix, Ariz.). The optics module and detector included a UV light source (deuterium lamp) and a 214 nm wavelength filter on a rotating wheel, and a detector that aligns with the aperture of the window, which is located 6.5 cm from the outlet of the tube. The detection wavelength was 214 nm at 24° C. The injection mode was a 10 second pressure injection. The separation voltage was 10 kV and the separation time was eight minutes.

Each capillary was rinsed with 150 mM borate buffer, pH 10.5 (running buffer) for 1.5 minutes, followed by equilibration of the capillary in the running buffer for 0.5 minute. Next the sample was injected by a ten second pressure injection, followed by the 8 minute separation at 10 kV. The capillary was then rinsed with 1N NaOH for one minute and then rinsed again with distilled water for one minute.

As shown in FIG. 1, the pH 7.3 succinylated antibody was a heterogeneous mixture of at least two antibodies with different degrees of succinylation. Thus, FIG. 1 shows one broad peak at a migration time of about 1.8 minute and a sharp spike at about 2.1 minute.

Example 2

(Protein succinylation at pH 10.9)

The experiment set forth in Example 1 was repeated under the same conditions, except that upon addition of the succinic anhydride, the pH of the reaction solution was immediately raised to and maintained at pH 10.9.

As shown by FIG. 1, the heterogenicity of the resulting modified antibody decreased. Thus, succinylation of a protein at a pH greater than about pH 10, and specifically at pH 10.9, can result in a less heterogeneous succinylated protein as compared to the modified polypeptide resulting from modification at pH 7.3.

Example 3

(One Step Protein Succinylation at pH 12.2)

This experiment sets forth a one step method, that is a method in which only one addition of succinic anhydride modifier is made to the antibody solution. The experiment set forth in Example 1 was repeated under the same conditions, except that upon addition of the succinic anhydride, the combined antibody and succinic anhydride reaction solution was raised to and maintained at pH 12.2 by dropwise addition of 1N NaOH throughout the succinylation reaction. The reaction was monitored by a pH meter. Completion of the succinylation reaction was indicated by stabilization of the pH of the reaction solution at pH 12.2. As soon as the pH of the reaction solution stabilized, the reaction solution was subjected to purification by ultrafiltration to remove residual succinic and to equilibrate the solution in the protein diluent. The succinylated antibody was analyzed by capillary electrophoresis.

As shown by FIG. 1, the pH 12.2 succinylated antibody was homogeneous, as demonstrated by capillary electrophoresis. The migration time of the modified antibody was between 2.3 and 2.4 minutes.

Example 4

(Two Step Protein Succinylation at pH 12.2)

This experiment sets forth a two step method, that is a method in which two separate additions of succinic anhydride are made to the antibody solution.

To 1 ml of antibody solution in the protein diluent (10 mg/ml protein diluent) containing 0.06 μmoles of antibody, a 2 μl solution containing 2 μmoles of succinic anhydride in DMF (0.1 mg succinic anhydride/μl DMF) was added. The ratio of succinic anhydride to antibody used was therefore about 33:1. The pH of this reaction solution was immediately adjusted and maintained at pH 12.2 by dropwise addition of 1N NaOH throughout the succinylation reaction. The pH of the reaction solution was monitored by a pH meter, and the completion of the succinylation reaction was indicated by stabilization of the pH of the reaction solution at 12.2. Once the pH had stabilized at 12.2, sufficient 1N HCL solution was added to lower the pH of the reaction solution to between pH 6.3–7.0.

A second aliquot (4 μl) of the succinic anhydride solution (0.1 mg succinic anhydride/μl DMF) was then added to the reaction solution. Thus, the ratio of succinic anhydride to antibody used was therefore about 67:1. Hence the total ratio of succinic anhydride to antibody used was about 100:1. The pH of the reaction solution was then immediately raised and maintained at pH 12.2 by dropwise addition of 1N NaOH until the pH stabilized at pH 12.2. The solution was then diluted with the protein diluent to a protein concentration of between 1–2 mg/ml and was subjected to ultrafiltration to remove residual succinic anhydride and to equilibrate the solution in the protein diluent.

Figure 2:
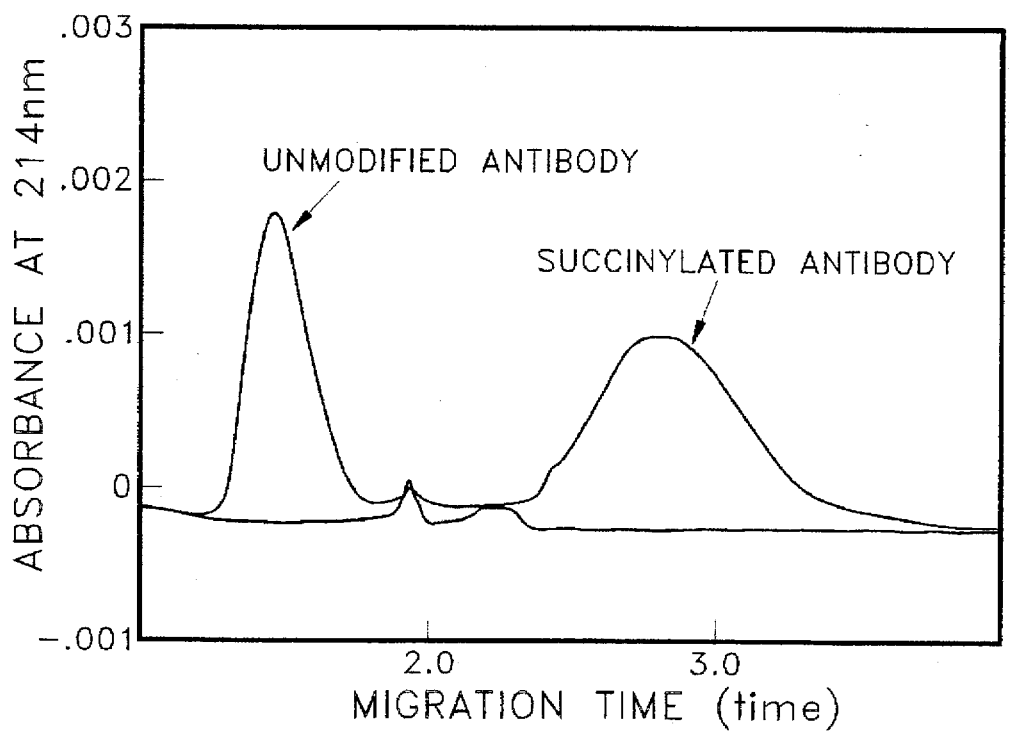
FIG. 2 is a capillary electropherogram resulting from analysis of an aliquot of a solution of anti-IgG antibody succinylated by a second method according to the present invention where two separate additions of succinic anhydride were made to the anti-IgG antibody solution and the succinylation was carried out at pH 12.2

Analysis was then carried out by capillary electrophoresis upon the succinylated antibody resulting from this experiment and upon a sample of unmodified antibody which had not been subjected to any succinylation procedure. The resulting electropherograms are shown by FIG. 2. The unmodified antibody had a migration time of about 1.5 minutes. The two step, pH 12.2 modified antibody had a migration time of about 2.8 minutes. Thus, the succinylated antibody resulting from this experiment migrated anodically in the capillary electrophoresis system as a symmetrical peak and was more negatively charged than either the unmodified antibody or the succinylated antibody of Example 3.

Thus, it can be concluded that the succinylated protein made by the pH 12 two step method of this experiment was more highly modified (that is more of the total free amino groups per protein molecule were succinylated), as shown by the higher migration time, than either the pH 7.3 method succinylated antibody, the pH 10.9 method succinylated antibody, or the pH 12.2 single step method succinylated antibody.

The result of this experiment also show that this two step pH 12 succinylation method produces a homogeneous succinylated protein, as a single electropherogram peak was recorded.

The two step method set forth in this Example was also used to prepare: a homogeneous succinylated anti-IgM antibody (single capillary electropherogram peak, migration time of about 2.4 minutes); a homogeneous succinylated anti-IgA antibody (single capillary electropherogram peak, migration time of about 2.6 minutes); a homogeneous succinylated anti-kappa antibody (single capillary electropherogram peak, migration time of about 2.6 minutes); and a homogeneous succinylated anti-lambda antibody (single capillary electropherogram peak, migration time of about 2.3 minutes).

Example 5

(Immunological Activity of the Succinylated Protein)

An experiment was conducted to determine if the succinylated protein made by the two step method of Example 3 retained its immunological activity.

Figure 3:
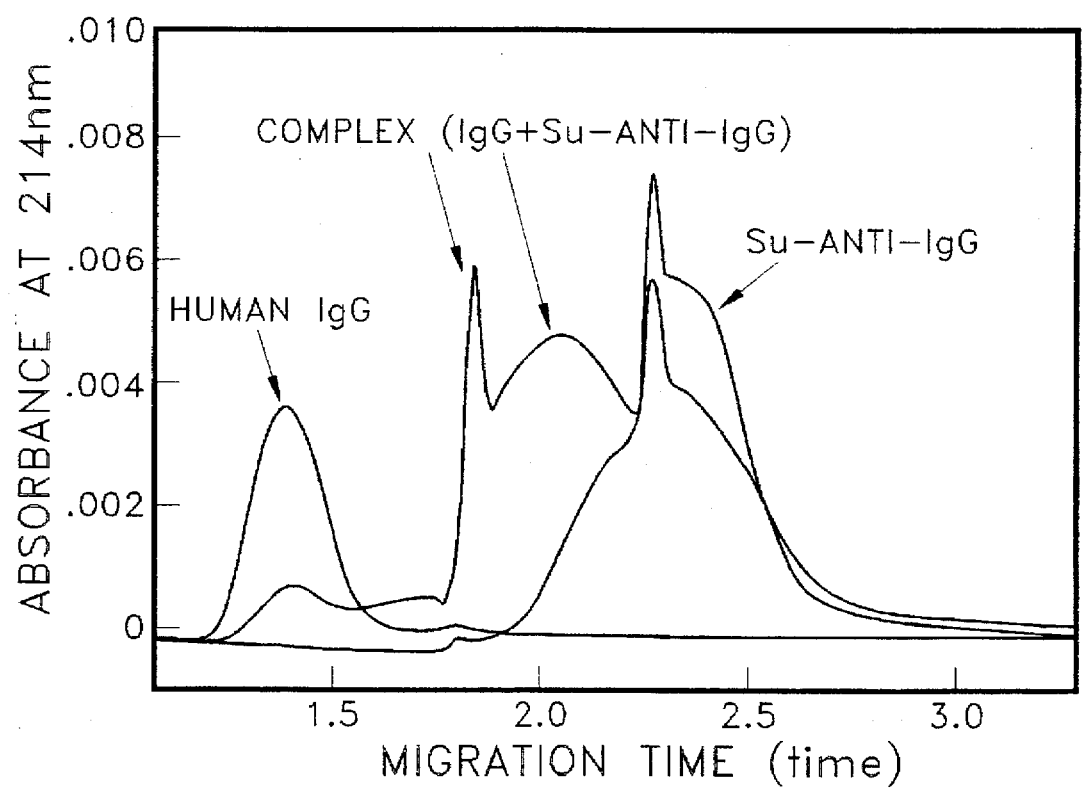
FIG. 3 is a capillary electropherogram resulting from analysis of an aliquot of a solution of anti-IgG antibody succinylated by the second method of the present invention and shows retention of immunological characteristics by the succinylated antibody.

Goat anti-human IgG antibody was succinylated according to the two step method of Example 3. The succinylated antibody was then incubated with human IgG, followed by capillary electrophoresis. Human IgG and succinylated human IgG were also analyzed by capillary electrophoresis and the results are shown by FIG. 3. FIG. 3 shows that the IgG-succinylated anti-IgG complex migrated between the IgG and the succinylated anti-IgG. Hence the succinylated anti-IgG retained its immunological binding activity.

The present invention has many advantages including the following:

1. homogeneously modified protein can be obtained by either a one or two step method carried out at about pH 12.

2. the two step pH 12 method can make homogeneous modified protein in ten minutes or less.

3. the homogeneously modified succinylated antibodies have excellent lot-to-lot reproducibility of immunological characteristics.

4. the disclosed methods can be used in all areas where proteins need to be succinylated or otherwise acylated.

Although the present invention has been described in detail with regard to certain preferred methods, other embodiments, versions, and modifications within the scope of the present invention are possible. For example, a wide variety of polypeptides can be homogeneously modified by the disclosed methods. Additionally, polyamines such as putrescine, spermine, and spermidine can be homogeneously succinylated by practising the present invention.

Furthermore, the invention can be used to prepare a wide variety of homogeneously modified polypeptides which retain their immunological activity. Accordingly, the spirit and scope of the following claims should not be limited to the descriptions of the preferred embodiments set forth above.

We claim:

1. A method for making a polypeptide derivative, comprising the steps of:
   (a) adding a polypeptide modifier comprising an acyl group to a polypeptide solution;
   (b) followed by adjusting the pH of the polypeptide solution to a pH of at least about 10 to thereby obtain a solution comprising a homogeneous acylated polypeptide derivative.

2. The method of claim 1, wherein the pH is adjusted to a pH of between about pH 10 and about pH 12.5.

3. The method of claim 1, wherein the pH is adjusted to a pH of between about pH 11 and about pH 12.5.

4. The method of claim 1, wherein the pH is adjusted to a pH of between about pH 12 and about pH 12.2.

5. The method of claim 1, wherein the polypeptide solution is maintained at a temperature of between about 4° C. and about 40° C.

6. The method of claim 1, wherein during the method the polypeptide solution is maintained at a temperature of between about 15° C. and about 25° C.

7. The method of claim 1, wherein a time period of between about thirty seconds and about thirty minutes elapses form initiation of the adding step and completion of the adjusting step.

8. The method of claim 1, wherein a time period of between about five minutes and about twenty minutes elapses from initiation of the adding step to completion of the adjusting step.

9. The method of claim 1, wherein a time period of about ten minutes elapses initiation of the adding step to completion of the adjusting step.

10. The method of claim 1, wherein a time period of between about thirty seconds and about ten minutes elapses between initiation of the adjusting step and termination of the adjusting step.

11. The method of claim 1, wherein a time period of between about thirty seconds and about five minutes elapses between initiation of the adjusting step and termination of the adjusting step.

12. The method of claim 1, wherein the polypeptide modifier comprises a succinyl-containing compound.

13. The method of claim 1, wherein during the adding step a stoichiometric excess of the polypeptide modifier is added to the polypeptide solution as compared to the amount of polypeptide present in the polypeptide solution.

14. The method of claim 1, further comprising the step of removing the homogeneous acylated polypeptide derivative from the solution.

15. The method of claim 1, further comprising the additional steps after the adjusting step of:
   (a) lowering the pH of the polypeptide solution; and
   (b) repeating steps (a) and (b) of claim 1.

16. A method for making a homogeneous polypeptide derivative, comprising the steps of:
   (a) adding a stoichiometric excess of a polypeptide free amino group modifier to a solution comprising a polypeptide, wherein the polypeptide solution is maintained at a temperature of between about 4° C. and about 40° C.;
   (b) reacting the polypeptide free amino group modifier with the polypeptide in the solution in an acylation reaction; and
   (c) followed by adjusting the pH of the polypeptide solution to a pH of between about pH 10 and about pH 12.5, to facilitate reaction between the polypeptide free amino group modifier and the polypeptide, thereby making a homogeneous polypeptide derivative.

17. The method of claim 16, wherein the reaction between the modifier and the polypeptide is essentially complete upon completion of the adjusting step.

18. A method for making a homogeneous succinylated polypeptide derivative, comprising the steps of:
   (a) adding a succinyl-containing compound to a polypeptide solution to form a mixture;
   (b) followed by adjusting the pH of the mixture to a pH of between about pH 10 and about pH 12.5, thereby obtaining a solution comprising a homogeneous succinylated polypeptide;
   (c) lowering a pH of the solution to a pH between about pH 6 and pH 7;
   (d) adding additional succinyl-containing compound to the polypeptide solution; and
   (e) followed by raising the pH of the polypeptide solution to a pH of between about pH 10 and about pH 12.5, to thereby obtain a solution comprising a homogeneous succinylated polypeptide succinylated to a greater degree that the homogeneous succinylated resulting from step (b) above, wherein throughout the method the polypeptide solution is maintained at a temperature of between about 4° C. and about 40° C.

* * * * *